United States Patent [19]

Abou-Gharbia et al.

[11] Patent Number: 4,716,165
[45] Date of Patent: Dec. 29, 1987

[54] HISTAMINE $H_1$ ANTAGONISTS

[75] Inventors: Magid A. Abou-Gharbia, Brandywood; Susan T. Nielsen, Wilmington, both of Del.

[73] Assignee: American Home Products Corporation, New York, N.Y.

[21] Appl. No.: 910,906

[22] Filed: Sep. 24, 1986

[51] Int. Cl.$^4$ .................. C07D 473/08; A61K 31/52
[52] U.S. Cl. .................. 514/265; 544/268; 544/269
[58] Field of Search ............. 544/276, 277, 268, 267, 544/269; 514/265

[56] References Cited

U.S. PATENT DOCUMENTS 4,426,383 1/1984 Sugimoto et al. .................. 424/253
4,493,837 1/1985 Sugimoto et al. .................. 544/269
4,603,204 7/1986 Thiele et al. .................. 544/268

Primary Examiner—Nicholas S. Rizzo
Attorney, Agent, or Firm—Richard K. Jackson

[57] ABSTRACT

Histamine $H_1$ antagonists of the formula:

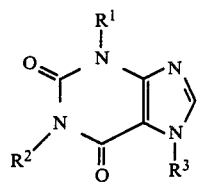

in which
$R^1$ is hydrogen or alkyl of 1 to 6 carbon atoms;

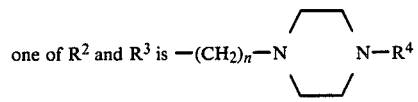

one of $R^2$ and $R^3$ is $-(CH_2)_n-N\phantom{x}N-R^4$ and the other is hydrogen or alkyl of 1 to 6 carbon atoms, where

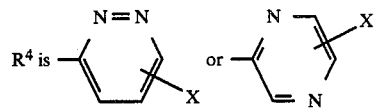

$R^4$ is in which X is hydrogen, alkyl of 1 to 6 carbon atoms, alkoxy of 1 to 6 carbon atoms, halo, cyano or a nitro substituent on one of the available carbon atoms; and
n is one of the integers 2, 3 or 4;
or a pharmaceutically acceptable salt thereof.

9 Claims, No Drawings

HISTAMINE H₁ ANTAGONISTS

BACKGROUND OF THE INVENTION

U.S. Patent Ser. No. 4,426,383 discloses a group of theophylline derivatives which serve as vasodilators useful for increasing blood flow in the treatment of circulatory insufficiency. The compounds are also disclosed to control blood platelet aggregation, act on the central nervous system (psychic energizers), provide antihistamine, analgesic, anti-asthmatic and hypotensive actions.

DESCRIPTION OF THE INVENTION

In accordance with this invention there is provided a group of histamine H₁ antagonists of the formula:

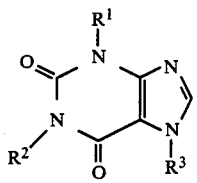

in which

R¹ is hydrogen or alkyl of 1 to 6 carbon atoms;

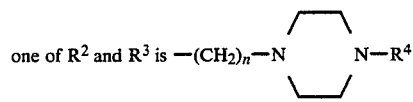

and the other is hydrogen or alkyl of 1 to 6 carbon atoms, where

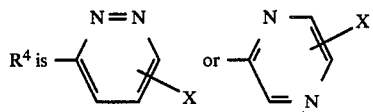

in which X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;
or a pharmaceutically acceptable salt thereof.

Of these compounds, the theophylline derivatives are preferred and present the following group of compounds:

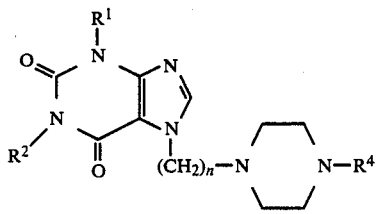

in which

R¹ and R² are, independently, hydrogen or alkyl of 1 to 6 carbon atoms;

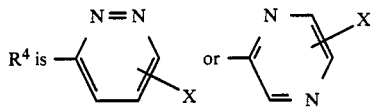

where X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;
or a pharmaceutically acceptable salt thereof.

The compounds of this invention may be prepared by a variety of synthetic routes using conventional methods. Thus, compounds in which R¹ and R² are methyl and R³ is substituted piperazinylalkyl can be prepared by reacting theophylline with dihaloalkane to yield a theophylline alkyl halide intermediate which then reacted with the appropriately substituted piperazine in the presence of triethylamine in DMF as illustrated by the following equation:

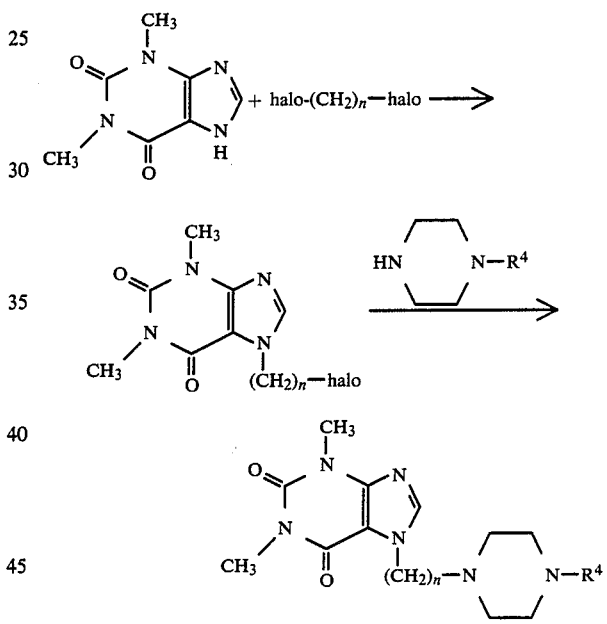

The theobromine derivatives may be similarly prepared.

The pharmaceutically acceptable salts of the antihistaminic agents of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention were established to be histamine H₁ antagonists by subjecting them to the following standard test procedure for H₁-blocking activity:

Fresh segments of terminal ileum immediately proximal to Peyer's patch obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1\times10^{-7}$M. The response was noted as grams tension. Test drug was added, in the presence of histamine, to each bath to a final concentration of $1 \times 10^{-6}$M. The change in grams tension was noted and the percent reduction in grams tension calculated.

The results obtained in accordance with this procedure established that the compounds exemplified, infra, exhibit a potent, competitive antagonist action against the histamine-induced contractile response in the isolated guinea pig ileum, thereby establishing them as histamine $H_1$ antagonists. This activity is illustrated by the compound of Example 1 which produced 50 percent inhibition of the contractile response at $10^{-6}$M concentration. The compound of Example 2 gave a 29 percent antagonist action against the histamine-induced contractile response at a $10^{-7}$M concentration.

The pharmacological results obtained characterize the compounds of this invention as $H_1$-receptor antagonists useful in the treatment of conditions such as asthma, hay fever, allergic rhinitis, atopic dermatitis and eczema. As such, they may be administered topically or systemically. Topical administration is advantageously achieved to the skin via creams, ointments or lotions, or via aerosol introduction into the respiratory tract. Synthetic administration may be orally, parenterally or rectally. In each instance, conventional formulations amenable to use in the desired administration route is appropriate. Hence, tablets and capsules may be prepared for oral administration and isotonic aqueous solutions for intravenous, subcutaneous or intramuscular injection.

As is conventional in the use of antihistaminic agents, the appropriate dosage is determined on a subjective basis by initial administration of small amounts, ca. 1–15 mg., followed by increasing quantities up to about 400 mg. by topical, oral, or rectal routes and about 200 mg. intravenous, until the desired symptomatic relief is obtained. The dosage is personalized in this manner for each patient, based upon size, age, type of discomfort, degree of disability etc. by the physician.

The following example is presented to illustrate the preparation of representative compounds of the invention.

EXAMPLE 1

7-[3-[4-(6-chloro-3-pyridazinyl)-1-piperazinyl]propyl]-3,7-dihydro-1,3-dimethyl-1H-purine-2,6-dione A solution of 0.45 g. (0.019 mol) of sodium hydride (prepared from 0.76 g. of 60% sodium hydride in mineral oil by pentane washing) in 50 ml. of dimethylformamide is treated portionwise with 3.4 g. (0.01 mol) of theophylline.

The resulting solution is added dropwise to a stirred solution of 15 g. (0.07 mol) of 1,3-dibromopropane in 40 ml. of dimethylformamide. The reaction mixture is stirred overnight and the solvent is removed under vacuum and the residue partitioned between methylene chloride and water.

The combined methylene chloride extracts are washed with brine and dried over anhydrous $Na_2SO_4$. Filtration and removal of the solvent in vacuo affords 4 g. (74% yield) of 7-(3-bromopropyl)-3,7-dihydro-1,3-dimethyl-1H-purine-2,6-dione as a waxy solid.

The title compound was prepared by adding to a stirred solution of 2 g. (0.006 mol) of 7-(3-bromopropyl)-3,7-dihydro-1,3-dimethyl-1H-purine-2,6-dione in 50 ml. of dimethylformamide, 4 ml. of triethylamine and 1.77 g. (0.006 ml.) of 1-(6-chloro-3-pyridazinyl)piperazine hydrochloride. The reaction mixture is stirred overnight and the solvent is removed under reduced pressure and then is partitioned between water and methylene chloride. The methylene chloride extracts are combined, dried over anhydrous $Na_2SO_4$, filtered and rotoevaporated to give crude free base. Preparative HPLC (silica gel, ethylacetate, methylene chloride, 9:1) followed by evaporation of the appropriate fractions (TLC $R_f$=0.2), treatment with ethanolic hydrogenchloride and recrystallization from ethanol gives the titled compound as the dihydrochloride, sesquihydrate; m.p. 297°–300° C.

Analysis for: $C_{18}H_{23}ClO_2.2HCl.1\frac{1}{2}H_2O$ Calculated: C, 41.65; H, 5.20; N, 21.60 Found: C, 41.55; H, 4.92; N, 21.85

EXAMPLE 2

7-[3-[4-(6-chloro-2-pyrazinyl)-1-piperazinyl]propyl]-3,7-dihydro-1,3-dimethyl-1H-purine-2,6-dione The title compound was prepared following the procedure of Example 1 with the exception that 1-(6-chloro-2-pyrazinyl)piperazine hydrochloride was used instead of 1-(6-chloro-3-pyridazinyl)piperazine hydrochloride. The product was converted to the hydrochloride salt and recovered as a monohydrate; m.p. 254°–256° C.

Analysis for: $C_{18}H_{23}ClN_5O_2.HCl.H_2O$ Calculated: C, 45.66; H, 5.49; N, 23.67 Found: C, 45.66; H, 5.18; N, 22.97.

EXAMPLE 3

1-[3-[4(6-chloro-3-pyridazinyl)-1-piperazinyl]propyl]-3,7-dihydro-3,7-dimethyl-1H-purine-2,6-dione The title compound was prepared following the procedure of Example 1 with the exception that theobromine was used instead of theophylline. The product was convered to the trihydrochloride salt and recovered as a monohydrate; m.p. 285°–287° C.

Analysis for: $C_{18}H_{23}ClN_8O_2.3HCl.H_2O$ Calculated: C, 39.56; H, 5.12; N, 20.51 Found: C, 39.59; H, 5.00; N, 20.45.

EXAMPLE 4

7-[3-[4-(3-chloro-2-pyrazinyl)-1-piperazinyl]propyl]-3,7-dihydro-1,3-dimethyl-1H-purine-2,6-dione The title compound was prepared following the procedure of Example 1 with the exception that 1-(3-chloro-2-pyrazinyl)piperazine was used instead of 1-(6-chloro-3-pyridazinyl)piperazine hydrochloride. The product was converted to the dihydrochloride salt and recovered as a dihydrate; m.p. 205°–207° C.

Analysis for: $C_{18}H_{23}ClN_5O_2.2HCl.2H_2O$ Calculated: C, 40.95; H, 5.49; N, 21.23 Found: C, 41.15; H, 5.37; N, 21.08.

What is claimed is:

1. A compound of the formula:

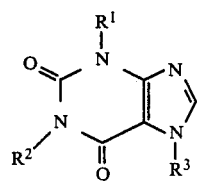

in which $R^1$ is hydrogen or alkyl of 1 to 6 carbon atoms;

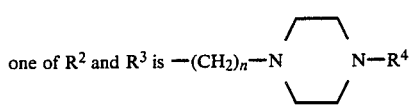

and the other is hydrogen or alkyl of 1 to 6 carbon atoms, where

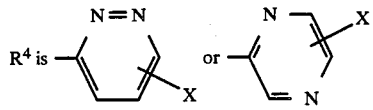

in which X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;

or a pharmaceutically acceptable salt thereof.

2. A compound of the formula:

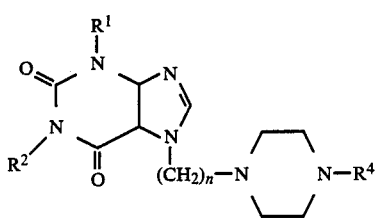

in which $R^1$ and $R^2$ are independently hydrogen or alkyl of 1 to 6 carbon atoms;

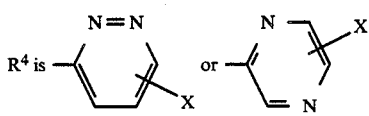

where X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;

or a pharmaceutically acceptable salt thereof.

3. A compound of claim 1 of the formula:

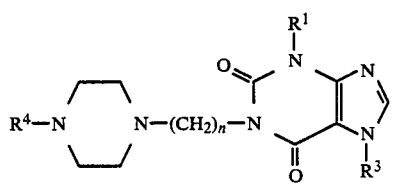

in which $R^1$ and $R^3$ are, independently, hydrogen or alkyl of 1 to 6 carbon atoms;

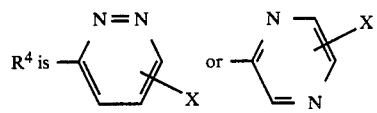

where X is hydrogen, alkyl of 1 to 6 carbon atoms, alkoxy of 1 to 6 carbon atoms, halo, cyano, or a nitro on one of the available carbon atoms; and n is one of the integers 2, 3 or 4;

or a pharmaceutically acceptable salt thereof.

4. The compound of claim 2 which is 7-[3-[4-(6-chloro-3-pyridazinyl)-1-piperazinyl]propyl]-3,7-dihydro-1,3-dimethyl-1H-purine-2,6-dione or a pharmaceutically acceptable salt thereof.

5. The compound of claim 2 which is 7-[3-[4-(6-chloro-2-pyrazinyl)-1-piperazinyl]propyl]-3,7-dihydro-1,3-dimethyl-1H-purine-2,6-dione or a pharmaceutically acceptable salt thereof.

6. The compound of claim 1 which is 1-[3-[4-(6-chloro-3-pyridazinyl)-1-piperazinyl]propyl]-3,7-dihydro-3,7-dimethyl-1H-purine-2,6-dione or a pharmaceutically acceptable salt thereof.

7. The compound of claim 2 which is 7-[3-[4-(3-chloro-2-pyrazinyl)-1-piperazinyl]propyl]-3,7-dihydro-1,3-dimethyl-1H-purine-2,6-dione or a pharmaceutically acceptable salt thereof.

8. A pharmaceutical composition comprising an antihistaminic amount of a compound of the formula:

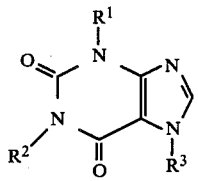

in which $R^1$ is hydrogen or alkyl of 1 to 6 carbon atoms;

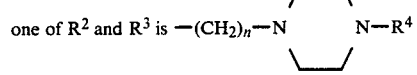

and the other is hydrogen or alkyl of 1 to 6 carbon atoms, where

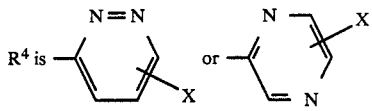

in which X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;

or a pharmaceutically acceptable salt thereof and a pharmaceutically acceptable carrier.

9. A process for antagonizing the effect of histamine at an $H_1$-receptor in a mammal in need of histamine antagonism which comprises administering to said mammal, orally or parenterally, a histamine $H_1$ antagonist amount of a compound of the formula:

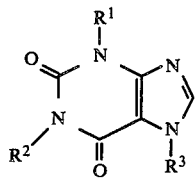

in which $R^1$ is hydrogen or alkyl of 1 to 6 carbon atoms;

one of $R^2$ and $R^3$ is 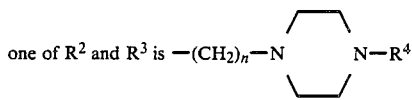

and the other is hydrogen or alkyl of 1 to 6 carbon atoms, where $R^4$ is 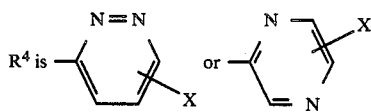

in which X is hydrogen, alkyl of 1 to 6 carbon atoms, alkoxy of 1 to 6 carbon atoms, halo, cyano or a nitro substituent on one of the available carbon atoms; and n is one of the integers 2, 3 or 4;

or a pharmaceutically acceptable salt thereof.

* * * * *